(12) United States Patent
Dumoulin (10) Patent No.: US 11,844,600 B2
(45) Date of Patent: *Dec. 19, 2023

(54) MRI TRANSFER STATION AND DOCK

(71) Applicant: Children's Hospital Medical Center, Cincinnati, OH (US)

(72) Inventor: Charles L Dumoulin, Cincinnati, OH (US)

(73) Assignee: CHILDREN'S HOSPITAL MEDICAL CENTER, Cincinnati, OH (US)

( * ) Notice: Subject to any disclaimer, the term of this patent is extended or adjusted under 35 U.S.C. 154(b) by 244 days.

This patent is subject to a terminal disclaimer.

(21) Appl. No.: 17/321,915

(22) Filed: May 17, 2021

(65) Prior Publication Data

US 2021/0267557 A1    Sep. 2, 2021

Related U.S. Application Data

(63) Continuation of application No. 16/029,621, filed on Jul. 8, 2018, now Pat. No. 11,033,200, which is a
(Continued)

(51) Int. Cl.
*A61B 5/05*  (2021.01)
*A61B 5/055* (2006.01)
(Continued)

(52) U.S. Cl.
CPC ............. *A61B 5/055* (2013.01); *A61B 5/416* (2013.01); *A61B 6/04* (2013.01); *A61G 7/103* (2013.01);
(Continued)

(58) Field of Classification Search
CPC .......... A61B 5/055; A61B 5/416; A61B 6/04; A61B 2503/045; A61G 7/103; A61G 13/1285

See application file for complete search history.

(56) References Cited

U.S. PATENT DOCUMENTS 4,665,364 A   5/1987 Hanawa
4,727,328 A   2/1988 Carper et al.
(Continued)

FOREIGN PATENT DOCUMENTS

WO   WO 1996/029932 A1   10/1996
WO   WO 2013/115846 A1   8/2013
(Continued)

OTHER PUBLICATIONS

Extended European Search report from EP application 12867342.3, dated Jul. 1, 2015; 7 pages.
(Continued)

*Primary Examiner* — Joel Lamprecht
(74) *Attorney, Agent, or Firm* — BakerHostetler (57) ABSTRACT

A patient table adapted for use in association with an MR scanner for neonatal infants is provided. The patient table has an extendable patient bed attached to and extendable from the patient table. The patient bed may be at least partially inserted into an MR scanner without requiring the patient table to enter the MR scanner. A transport mechanism is on the underside of the patient table so that it may be readily moved over the floor on which it rests. The patient table includes a latching mechanism that may operate to releasably attach the patient table to a patient table docking assembly. The docking assembly is operative to selectively move the patient table towards, into and away from the MR scanner.

20 Claims, 8 Drawing Sheets

Related U.S. Application Data continuation of application No. 14/376,544, filed as application No. PCT/US2012/052260 on Aug. 24, 2012, now Pat. No. 10,045,712.

(60) Provisional application No. 61/593,937, filed on Feb. 2, 2012.

(51) Int. Cl.
*A61G 7/10* (2006.01)
*A61B 6/04* (2006.01)
*A61G 13/12* (2006.01)
*A61B 5/00* (2006.01)

(52) U.S. Cl.
CPC .... *A61G 13/1285* (2013.01); *A61B 2503/045* (2013.01)

(56) References Cited

U.S. PATENT DOCUMENTS

| | | |
|---|---|---|
| 5,178,146 A | 1/1993 | Giese |
| 5,515,415 A | 5/1996 | Herrmann et al. |
| 5,619,763 A | 4/1997 | Randolph et al. |
| 5,650,724 A | 7/1997 | Yamagata |
| 5,724,970 A | 3/1998 | Votruba et al. |
| 5,792,041 A | 8/1998 | Kobayashi et al. |
| 5,800,335 A | 9/1998 | Koch et al. |
| 6,101,644 A | 8/2000 | Gagneur et al. |
| 6,377,047 B1 | 4/2002 | Wong et al. |
| 6,611,702 B2 | 8/2003 | Rohling et al. |
| 6,718,571 B2 | 4/2004 | Bartels |
| 6,854,140 B2 | 2/2005 | Bartels et al. |
| 7,093,311 B2 | 8/2006 | Gnoyke |
| 7,131,769 B2 | 11/2006 | Vezina |
| 7,216,383 B2 | 5/2007 | Heinl et al. |
| 7,467,004 B2 | 12/2008 | Calderon et al. |
| 7,599,728 B2 | 10/2009 | Feenan |
| 7,634,827 B2 | 12/2009 | Gagneur et al. |
| 7,827,635 B2 | 11/2010 | Wang et al. |
| 7,850,595 B2 | 12/2010 | White |
| 7,869,858 B2 | 1/2011 | Calderon et al. |
| 7,874,030 B2 | 1/2011 | Cho et al. |
| 7,920,910 B2 | 4/2011 | Calderon et al. |
| 8,147,396 B2 | 4/2012 | Srinivasan |
| 8,276,225 B2 | 10/2012 | Kogan et al. |
| 10,045,712 B2 * | 8/2018 | Dumoulin .......... A61G 13/1285 |
| 11,033,200 B2 * | 6/2021 | Dumoulin .............. A61G 7/103 |
| 2001/0052168 A1 | 12/2001 | Haase et al. |
| 2002/0104163 A1 | 8/2002 | Reimann |
| 2002/0158720 A1 | 10/2002 | Weyers et al. |
| 2002/0173717 A1 | 11/2002 | Rohling et al. |
| 2003/0153805 A1 | 8/2003 | Gryn et al. |
| 2005/0034237 A1 | 2/2005 | Lenting et al. |
| 2005/0113668 A1 | 5/2005 | Srinivasan |
| 2006/0293589 A1 | 12/2006 | Calderon et al. |
| 2007/0132581 A1 | 6/2007 | Molyneaux et al. |
| 2007/0232894 A1 | 10/2007 | Feenan |
| 2008/0117044 A1 | 5/2008 | Hibbs |
| 2008/0201849 A1 | 8/2008 | Van Es et al. |
| 2009/0009170 A1 | 1/2009 | Tigwell et al. |
| 2009/0027053 A1 | 1/2009 | Decke et al. |
| 2009/0083907 A1 | 4/2009 | Ahlman |
| 2010/0185045 A1 | 7/2010 | Chinn |
| 2011/0113555 A1 | 5/2011 | Smith |
| 2011/0145991 A1 | 6/2011 | Bridge et al. |
| 2012/0071745 A1 | 3/2012 | Rapoport |
| 2013/0025054 A1 | 1/2013 | Graw et al. |
| 2013/0109956 A1 | 5/2013 | Rapoport |
| 2013/0150656 A1 | 6/2013 | Falk et al. |

FOREIGN PATENT DOCUMENTS

| | | |
|---|---|---|
| WO | WO 2013/115847 A1 | 8/2013 |
| WO | WO 2013/115848 A1 | 8/2013 |

OTHER PUBLICATIONS

European Patent Application No. 12867263.1; Extended Search Report; dated Sep. 16, 2015; 7 pages.

Dumoulin, Charles L., et al., Magnetic Resonance Imaging Compatible Neonate Incubator, Magnetic Resonance Engineering, Jun. 28, 2002, vol. 15 (2), pp. 117-128.

PCT International Search Report/Written Opinion, PCT/US2012/052242, dated Nov. 2, 2012.

PCT International Search Report/Written Opinion, PCT/US2012/052249, dated Nov. 2, 2012.

PCT International Search Report/Written Opinion, PCT/US2012/052260, dated Nov. 2, 2012.

European Patent Application No. 12867132: Extended European Search Report dated Sep. 16, 2015, 6 pages.

European Patent Application No. 18202520.5; Extended Search Report; dated Jun. 11, 2019; 6 pages.

\* cited by examiner

MRI TRANSFER STATION AND DOCK

CROSS-REFERENCE TO RELATED APPLICATIONS

The present application is a continuation of U.S. patent application Ser. No. 16/029,621 filed Jul. 8, 2018, which is a continuation of U.S. patent application Ser. No. 14/376,544 filed Aug. 4, 2014, which is a national stage entry of International Application No. PCT/US2012/052260, which claims priority benefit of U.S. Provisional Patent Application Ser. No. 61/593,937 filed Feb. 2, 2012 and is further related to U.S. Provisional Patent Application Ser. No. 61/492,612 filed Jan. 4, 2011. All of the applications listed in this paragraph are incorporated herein by reference.

FIELD OF THE DISCLOSURE

The present disclosure relates generally to magnetic resonance imaging equipment suitable for use in neonatal care, and, more particularly, to an MRI transfer station and dock for receiving an infant from an incubator and to assist with preparing the infant for an MR scan.

BACKGROUND OF THE DISCLOSURE

Today premature infants weighing less than 1 kg may be stabilized and allowed to develop in neonatal intensive care units (NICUs). Magnetic resonance imaging (MRI) is a powerful technique for diagnostic purposes but is not routinely performed on these infants due to a number of technical and logistical challenges.

When a mother has a high-risk pregnancy, it is possible that the baby could be born prematurely and would require treatment in a neonatal intensive care unit or NICU. Also, unexpected early delivery may require that an infant be treated in an NICU.

One difficulty in utilizing MRI for these premature infants is monitoring the vital signs and life support of the infant during MR examination. Parameters that must be monitored during examination include electrolyte levels, hydration and temperature. A second difficulty in utilizing MRI is that the infant must be moved from an incubator or isolette into and out of the MR scanner. This movement places the infant at risk for injury.

Despite challenges, MRI has the potential to play an important diagnostic role in the care and management of neonates. The full use of this imaging technique requires that the imaging take place as early as the first few hours of life. At this stage, however, the infants are hemodynamically unstable. Accordingly, transporting and maintaining homeostasis in these fragile infants presents difficulty.

Another challenge in using MRI for neonates is that MRI systems are frequently located in Radiology departments outside of and perhaps distant from the NICU. Consequently, the neonate must be escorted out of the NICU. This may present certain logistical and technical challenges with respect to controlling the neonate's environment. Furthermore, removing staff from the NICU to transfer and attend to one baby outside the NICU can place the remaining babies in the NICU at increased risk of a reduced level of care due to decreased staff coverage.

An MR compatible transport incubator and imaging system has been developed (Dumoulin et. al.) and is currently in use. Concepts in Magnetic Resonance (Magnetic Resonance Engineering), Vol. 15(2) 117-128 (2002). This system is a self-contained MR compatible transport incubator which carries the infant from the NICU to an MR scanner located in or near the NICU. With this approach the baby must first be transferred from its "home" incubator or isolette in the NICU into the transport incubator. The transport incubator is then moved to the MR scanner where it is docked with the scanner. A portion of the transport incubator containing the baby is then moved into the center of the MR imaging system magnet where MR imaging is performed. While this approach has the advantage of not disturbing the baby while it is in the transport incubator, even during MR scanning, it has several limitations including: a) infants must be fully detached from the monitoring equipment in their home incubator to be transferred into the transport incubator, b) the MR system that is used for imaging must have a bore large enough to accommodate the portion of the transport incubator containing the baby (thereby requiring a large heavy magnet), c) the baby and its attending staff need to leave the NICU for scanning, and d) because the transport incubator must be fully MR compatible while providing full life support for the baby, the system is heavy and expensive.

An alternate approach to provide MR imaging to newborn babies has been disclosed by Feenan in U.S. Pat. No. 7,599,728. In this approach a relatively smaller MR magnet is employed and MR-compatible incubators are docked to the magnet thereby permitting the baby to be slid into the magnet for imaging. While this approach has the benefit of providing a magnet that is more easily installed in the NICU, it does have several limitations including the need for MR compatible incubators to be used throughout the NICU, or the transfer of a neonate from a non-MR-compatible home incubator to an MR-compatible incubator. This approach also limits the access to the attending staff as they prepare the infant for MR scanning. In particular, the staff must reach through the incubator to push the baby into and out of the magnet.

SUMMARY

A patient table adapted for use in association with an MR scanner for neonatal infants is disclosed. The patient table may include an extendable and moveable patient bed attached to a top surface of the patient table. The patient bed may include an extending mechanism that, when extended, causes the patient bed to be extended and at least partially project from the patient table. The patient bed may be dimensionally constructed such that it may be at least partially inserted into an MR scanner without requiring the patient table to enter the MR scanner. A transport mechanism, such as a set of wheels, may be attached to the underside of the patient table so that it may be readily moved over the floor on which the patient table rests. The patient table also includes a latching mechanism that may operate to releasably attach the patient table to a patient table docking assembly. The docking assembly may be operative to selectively move the patient table towards and away from the MR scanner.

The present disclosure will now be described in more detail with reference to exemplary embodiments thereof as shown in the accompanying drawings. While the present disclosure is described below with reference to exemplary embodiments, it should be understood that the present disclosure is not limited thereto. Those of ordinary skill in the art having access to the teachings herein will recognize additional implementations, modifications, and embodiments, as well as other fields of use, which are within the scope of the present disclosure as described herein, and with respect to which the present disclosure may be of significant utility.

BRIEF DESCRIPTION OF THE DRAWINGS

In order to facilitate a fuller understanding of the present disclosure, reference is now made to the accompanying drawings, in which like elements are referenced with like numerals. These drawings should not be construed as limiting the present disclosure, but are intended to be exemplary only.

DETAILED DESCRIPTION

The use of MRI techniques for infants, and in particular neonates, is highly desirable. MRI techniques provide diagnostic information without patient exposure to ionizing radiation, and are suitable for extended and repeated studies.

MR techniques provide excellent anatomic visualization and functional information. They can be used to measure neural fiber track development and have a number of potential clinical uses including, but not limited, to diagnosis of brain trauma, cardiac abnormalities, congenital defects and the assessment of lung development.

There are, however, a number of challenges in the use of MRI for neonatal imaging. Patient access during scanning can be difficult as MR magnets are typically large and surround the patient. Safety concerns include forces on ferromagnetic objects, potential for rf heating and acoustic noise. Also, logistics may be difficult, as MR scanners tend to be in radiology departments, while neonate infants are typically in the NICU.

FIGS. 1a-1d depict an exemplary MRI and incubator system 100 in or for which the techniques for the MR imaging of neonates in accordance with the present disclosure may be implemented. The illustrated MRI system comprises an MRI scanner 102. Since the components and operation of the MRI scanner are well-known in the art, only some basic components helpful in the understanding of the system 100 and its operation will be described herein.

Figure 1A:
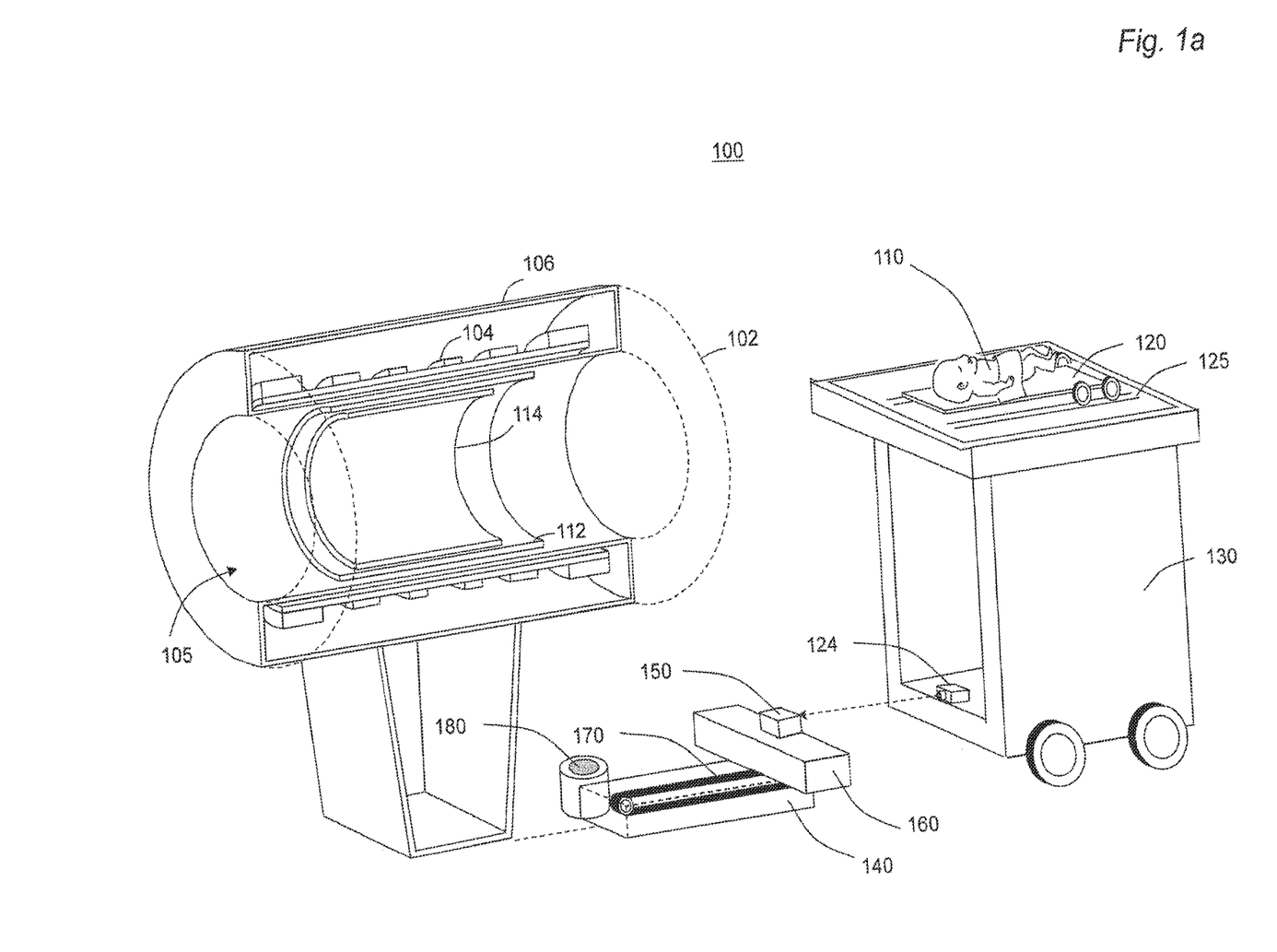
FIG. 1a is a perspective view showing an exemplary MR imaging system, an exemplary docking mechanism, and an exemplary patient table containing a neonate in accordance with the present disclosure.

The MRI scanner 102 may comprise a cylindrical superconducting magnet 104, which generates a static magnetic field within a bore 105 of the superconducting magnet 104. The superconducting magnet 104 generates a substantially homogeneous magnetic field within the magnet bore 105. The superconducting magnet 104 may be enclosed in a magnet housing 106.

A set of cylindrical magnetic field gradient coils 112 may also be provided within the magnet bore 105. The gradient coils 112 can generate magnetic field gradients of predetermined magnitudes, at predetermined times, and in three mutually orthogonal directions within the magnet bore 105. With the field gradients, different spatial locations can be associated with different precession frequencies, thereby giving an MR image its spatial resolution. An RF transmitter coil 114 is positioned within the gradient coils 112. The RF transmitter coil 114 emits RF energy in the form of a magnetic field for the purpose of exciting MR signals during image acquisition. The RF transmitter coil 114 can also receive MR response signals. The MR response signals are amplified, conditioned and digitized into raw data as is known by those of ordinary skill in the art.

The present disclosure provides an apparatus and a technique for safely and effectively transferring an infant from the primary care area to the MR magnet. In one particular embodiment, the present disclosure provides the means to transfer a neonate from the NICU to an MR magnet located either in a radiology department or in the NICU itself. The present disclosure accomplishes this by providing an MR-compatible transfer station that can be attached to the MR magnet. This station creates an MR compatible environment that, if desired the baby can be moved into without being detached from patient monitoring or life support systems. Once stabilized on the transfer station, the baby can then be moved into the magnet for imaging. Note that the in the present disclosure an incubator does not need to be fully MR compatible and can be constructed with some MR incompatible elements such as electrical motors.

Referring again to FIGS. 1a-1e, a patient table 130 containing a neonate 110 is shown. Neonate 110 may be placed on a moveable patient bed 120 attached to the top of patient table 130. Moveable patient bed 120 may be disposed on and may roll on a track 125. In alternate embodiments of the present disclosure the function of track 125 can be performed with alternate designs incorporating slides, cables, pulleys or the like. The patient table 130 may have wheels and may be designed to roll on the floor, so that the neonate can be placed on the patient table in a location remote from MRI scanner 102, such as near an incubator. Patient table 130 also have a latching mechanism 124 that may permit the patient table 130 to be temporarily and releasably attached to a docking assembly 140.

Figure 1B:
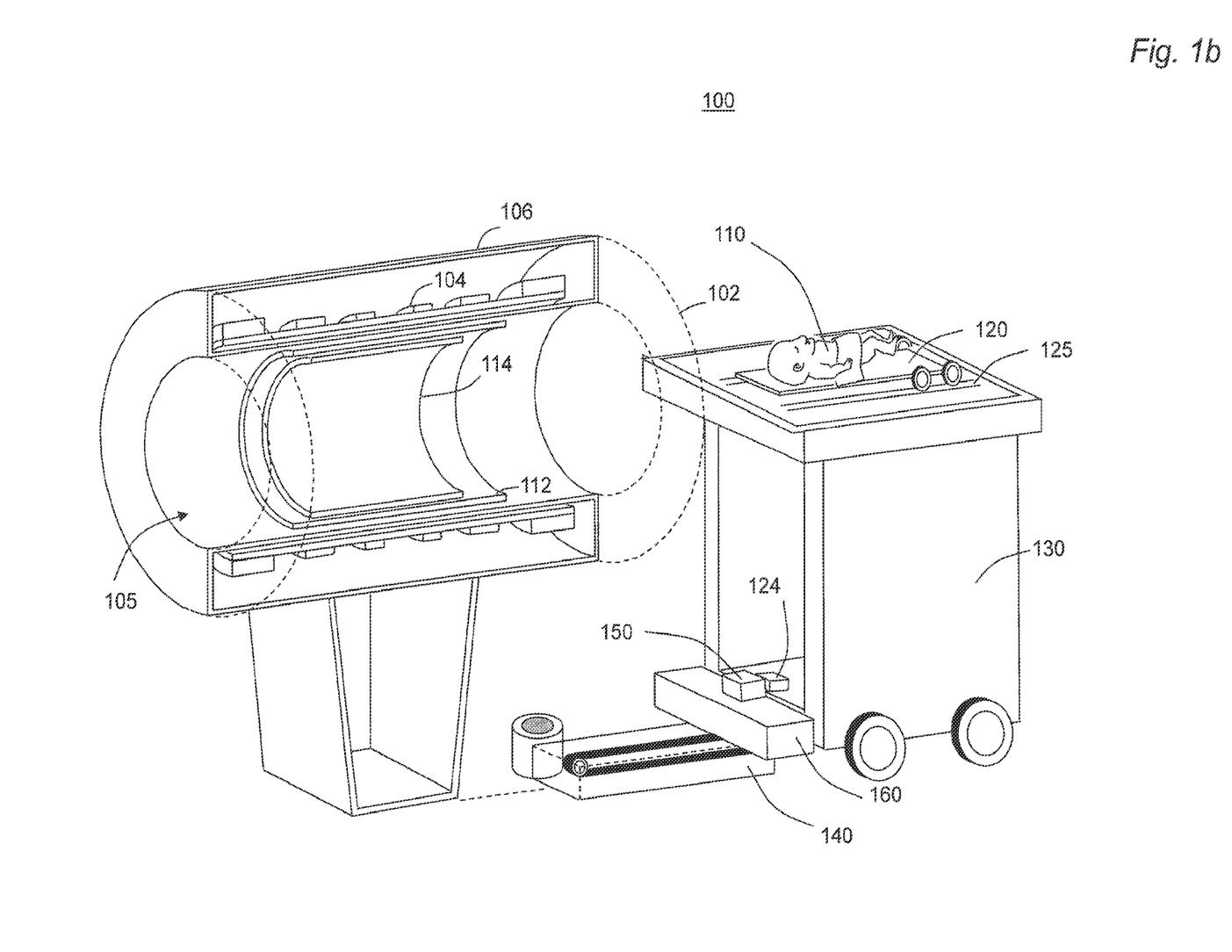
FIG. 1b is a perspective view showing the attachment of the patient table to a docking mechanism to prepare the neonate for movement in accordance with the present disclosure.

Docking assembly 140 may include a hitch mechanism 150 that may be attached to a moving tractor assembly 160. Moving tractor assembly 160 may be attached to a belt 170 which may be moved by a dock motor 180. Turns of the motor shaft may result in belt motion which in turn may cause the moving tractor assembly 160 to move relative to the fixed portion of docking assembly 140. In alternate embodiments of the present disclosure, the function of belt 170 may be accomplished with any suitable drive device as known in the art including but not limited to a screw drive, a chain drive, or a gear assembly.

FIG. 1b shows the docking of the patient table 130 to docking assembly 140. In the current embodiment of the disclosure latching mechanism 124 may engage hitch mechanism 150 and the two may then become coupled.

Decoupling of latching mechanism 124 and hitch mechanism 150 can be performed manually or automatically by the system when removal of patient table 130 from the vicinity of MRI scanner 102 is desired.

Figure 1C:
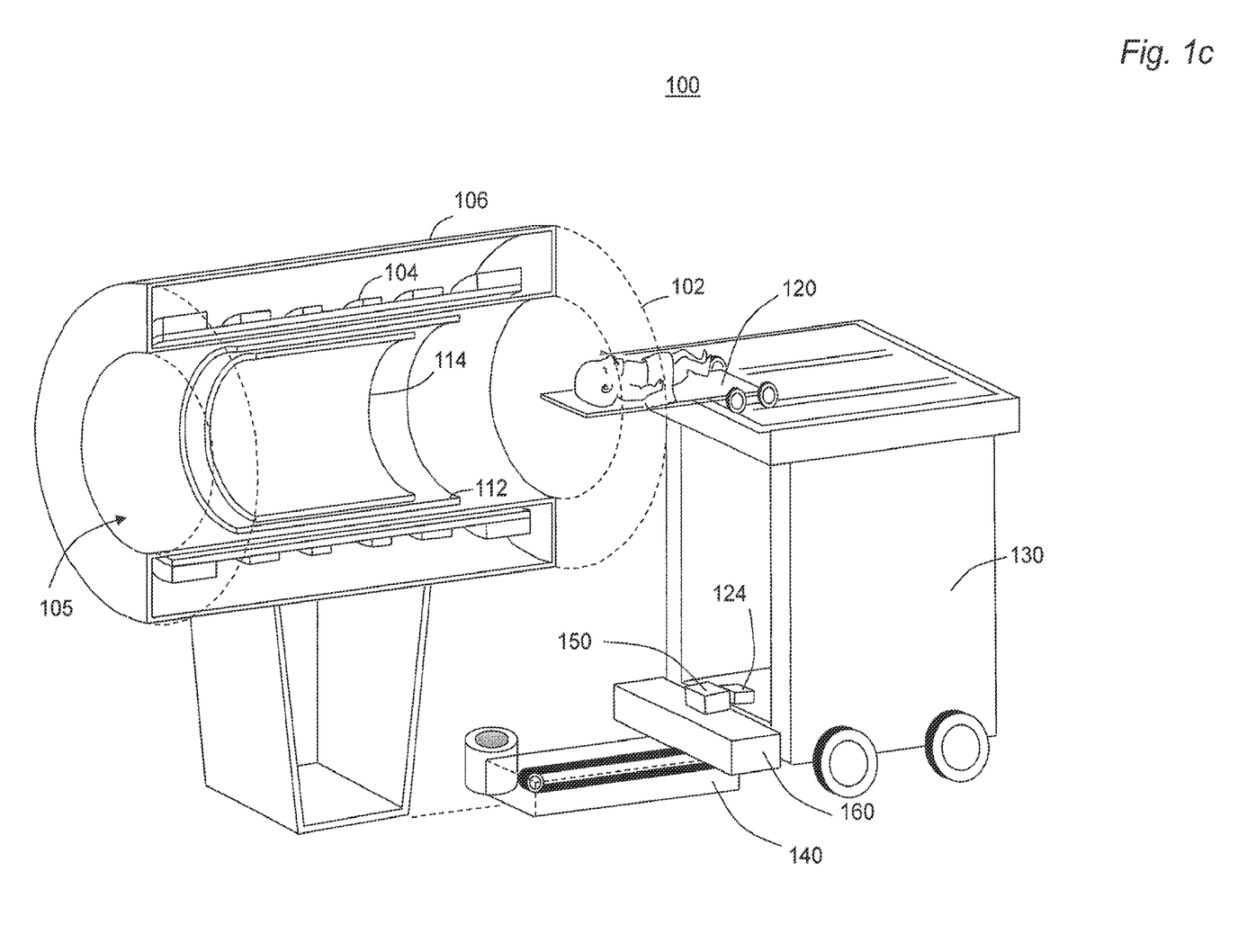
FIG. 1c is a perspective view showing the extension of the neonate on the MRI transfer station towards the magnet in the MR scanner.

FIG. 1c shows the extension of the neonate 110 and moveable patient bed 120 towards MRI scanner 102. In the current embodiment of the present disclosure, neonate 110 may be prepared for MR scanning while in this general location. Preparations may include safety checks, swaddling, attachment of additional monitoring equipment, placement of MR receive coils, and/or attachment of hearing protection to the neonate 110.

Figure 1D:
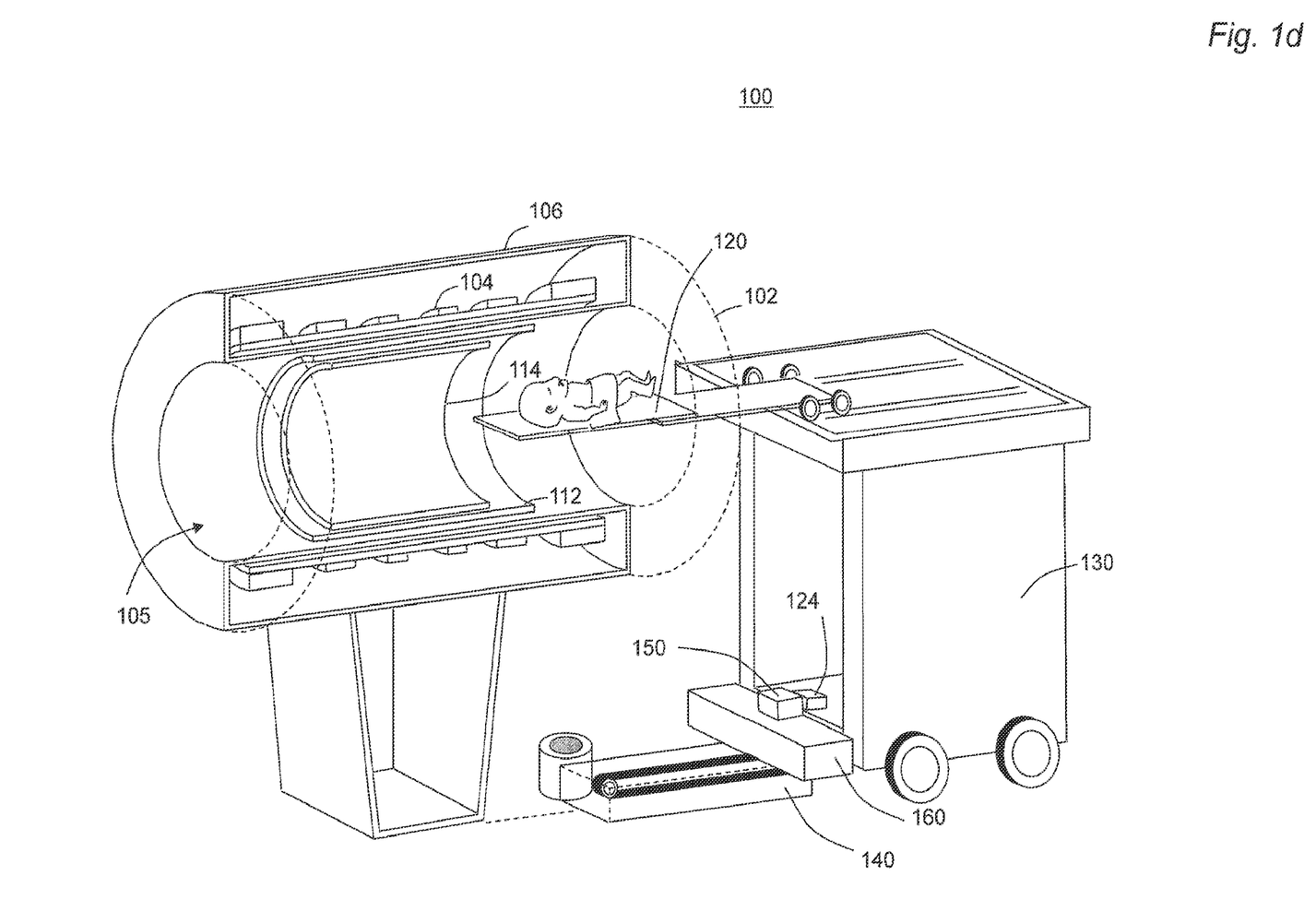
FIG. 1d is a perspective view showing a further extension of the neonate on the MRI transfer station towards the magnet in the MR scanner.

FIG. 1d shows the further extension of the neonate 110 and moving patient bed 120 into the MRI scanner 102. Note that during this extension the neonate is not moved with respect to moveable patient bed 120.

Figure 1E:
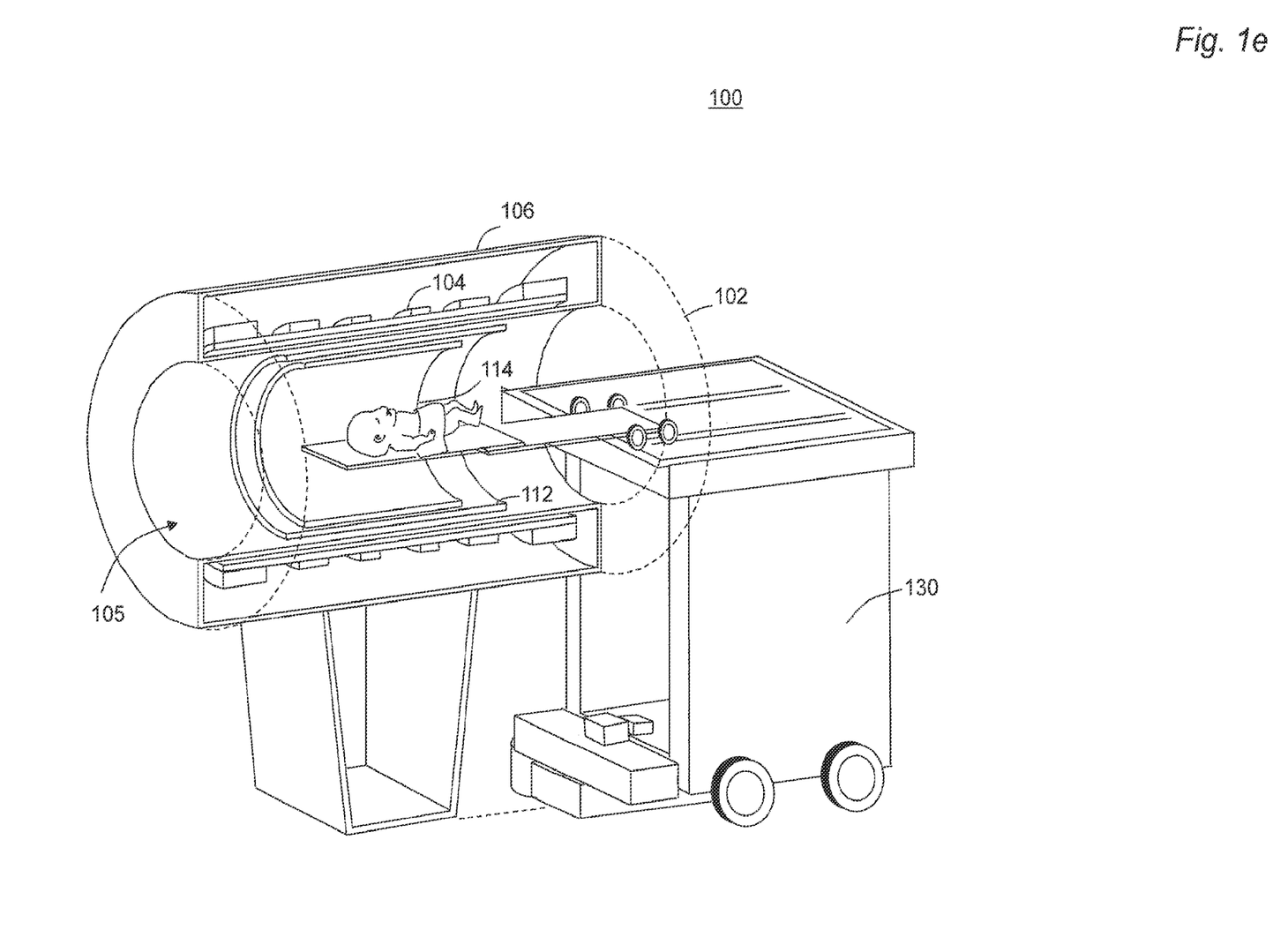
FIG. 1e is a perspective view that shows the movement of the neonate into the exemplary MR imaging system caused by motion of the docking mechanism that motion brings the patient table closer to the magnet and brings the neonate into the chamber of the MR scanner for imaging.

FIG. 1e shows the insertion of the neonate 110 and moving patient bed 120 into the MRI scanner 102. Note that during this insertion the neonate is not moved with respect to moveable patient bed 120, but may be placed in the imaging volume of MRI scanner 102.

Figure 2:
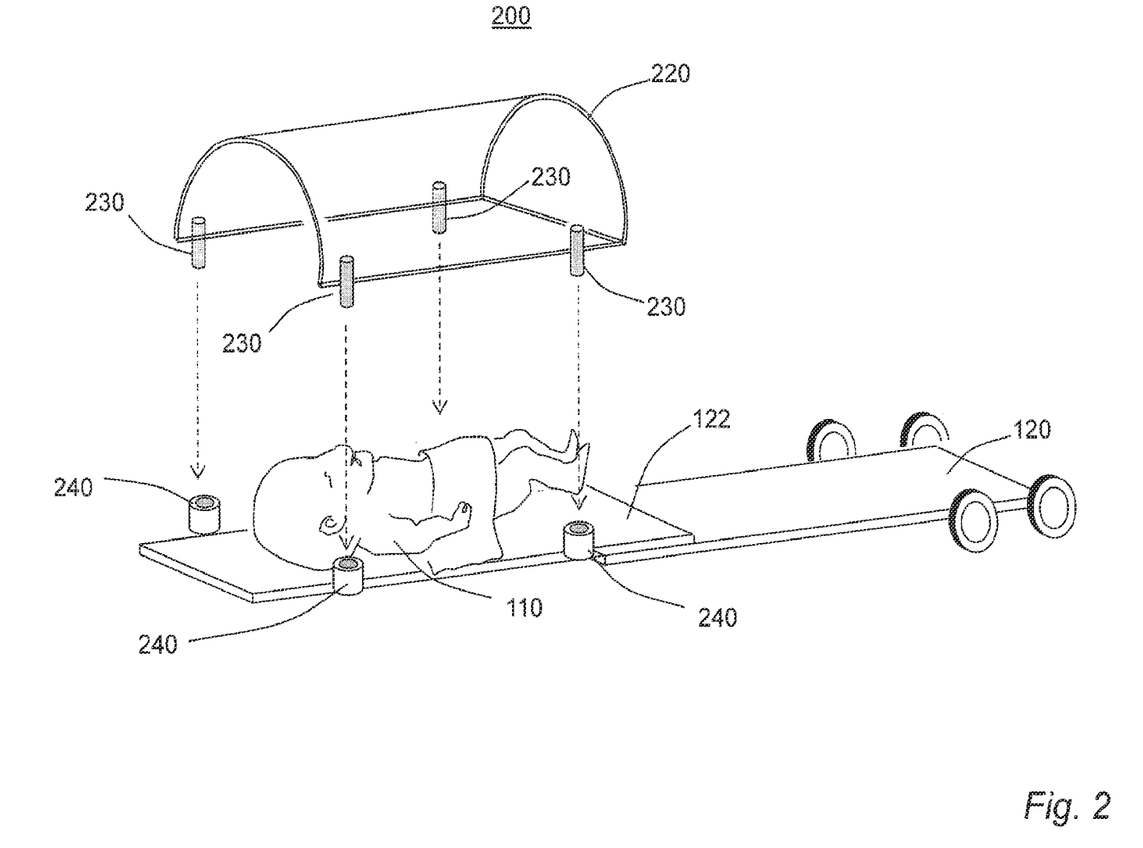
FIG. 2 is a perspective view of one embodiment of an MRI transfer station suitable for preparing a neonate for MR imaging.

FIG. 2 shows one embodiment of the moveable patient bed 120 in greater detail. Moving patient bed 120 may include a bed surface 122 and cover 220. The cover 220 may incorporate one or more cover locking pins 230 that are designed for insertion into a like number of corresponding cover pin sockets 240. The cover locking mechanism shown here is exemplary. It should be understood that alternate mechanisms for attaching the cover 220 to the moving patient bed 120, including but not limited to hinges, slots, clamps and slides. If desired, neonate access ports similar to those found in conventional neonate incubators can be incorporated into the cover 220. It should be obvious to one skilled in the art that patient table 130 and all subassemblies exposed to strong magnetic fields may be constructed using MR compatible materials.

The present disclosure is particularly advantageous in that it minimizes the transfer time from the NICU to MRI scanner 102 and provides less stress on the infant. Another advantage of the present disclosure is that babies do not need to be fully detached from patient monitoring equipment which can be integrated as desired into patient table 130. This further reduces preparation times and stress on the infant. Once the baby is stabilized, the baby and the patient table 130 can be inserted into the magnet to place the neonate 110 in the imaging region of the MRI scanner. This can be done manually by further extending moving patient bed 120 or under system control with appropriate driving of dock motor 180 to move patient table 130. This approach ensures that the local environment of the neonate 110 is not altered as it is brought into the center of the imaging system. Furthermore, because a transport incubator is not required to be fully inserted in the magnet, the MR magnet can be small and lightweight. This makes it more easily installed within the confines of the NICU, and provides improved access to MR for premature babies. In addition, the present disclosure permits MR scanning to be performed with fewer support personnel, and/or places support personnel closer to the other babies present in the NICU. With the present disclosure MR imaging can be made available to all babies in a NICU (typically between 10 and 60) using a single MR magnet and a single patient table that may be used for each compatible incubator in the NICU.

In particular, the present disclosure relates to a transfer station for preparing an infant, including neonates, prior to transfer into the magnet for imaging. The transfer station may have all of the functionality of the neonate's home incubator, but implemented in an MR-compatible and MR-safe manner.

Once the infant is on moveable patient bed 120, the infant can be prepared for MR scanning. As will be recognized by those skilled in the art of MR scanning, MR scanning frequently requires that several steps be performed before a patient can be inserted into an imaging magnet. These steps may include: a) immobilization of the patient (in the case of neonatal imaging, swaddling is frequently sufficient), b) the optional insertion of IV tubes for contrast injections, c) the attachment of MR imaging coils, d) a safety check to verify that no ferromagnetic objects are present, e) placement of hearing protection, and f) verification of patient stability and comfort. All of these steps need to be performed while the patient is near the magnet, and require access to the patient which is not possible with most incubator designs.

Another aspect of the moving patient bed 120 of the present disclosure is that it can provide full environmental control for the neonate when used with cover 220. Many neonates are too young to be able to fully control their internal temperature, and it is well known to those skilled in the art that small neonates must be kept warm. In the present disclosure, this can be done with warm air and/or a radiant heater driven by a temperature controller. In one embodiment of the disclosure, a thermocouple or similar temperature sensor modified for use in the MR environment with non-ferromagnetic parts and appropriate rf filtering may be used to provide feedback to the temperature controller to provide suitable temperature control. In another embodiment of the present disclosure a physiologic monitoring system may be utilized. This system may be MR compatible and MR safe. It can be used if desired in place of the patient monitoring systems found in the neonate's home incubator.

Figure 3:
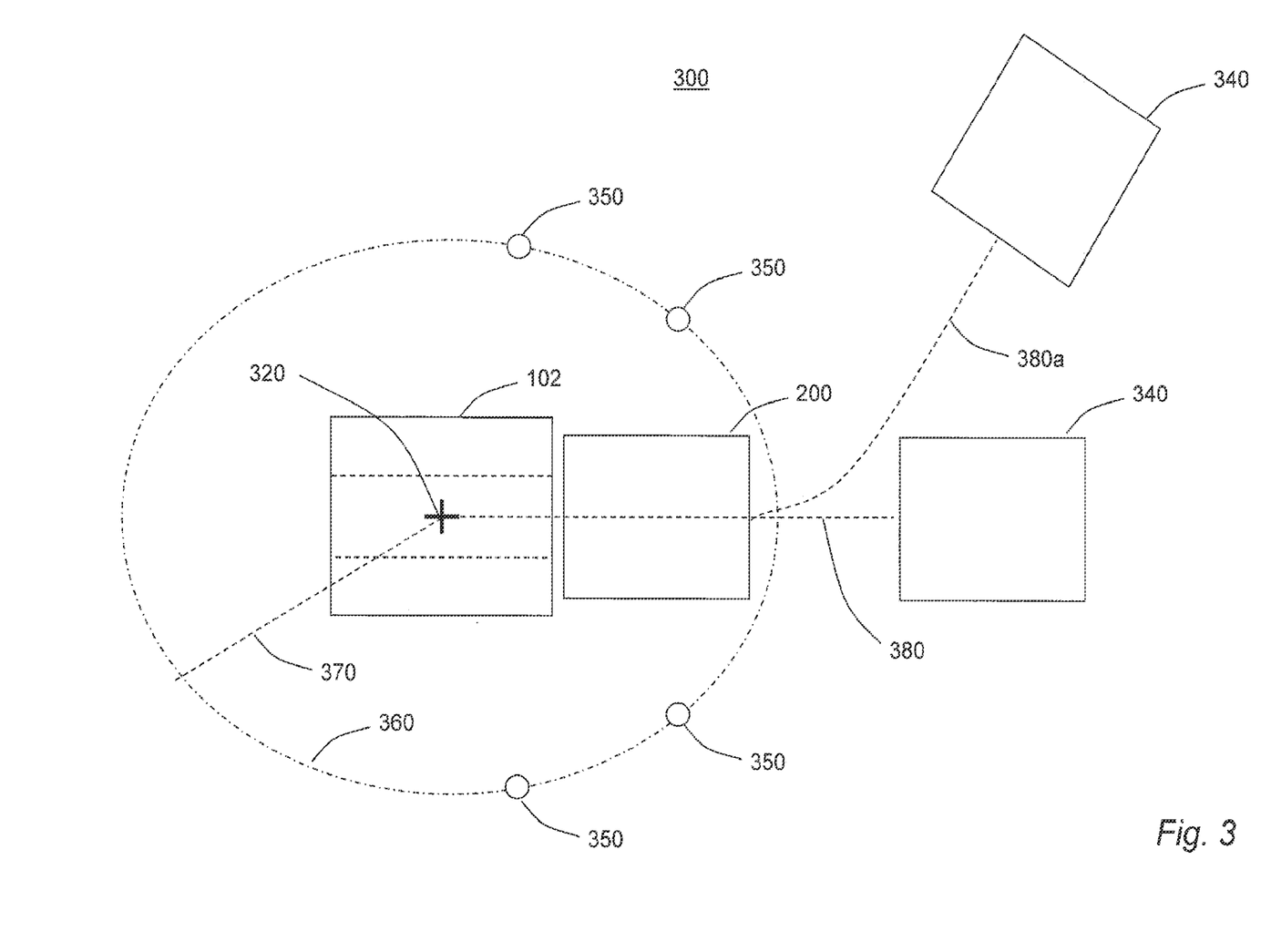
FIG. 3 is a top plan view of an exemplary MR magnet with barrier poles to limit access to the magnet.

As shown in FIG. 3, a safety barrier constructed with in-room barriers such as poles 350 in the floor may be used and may be spaced to prevent incubators or other devices from getting within a predetermined fringe magnetic field strength 360 (typically chosen to be 5 Gauss) at a selected distance 370 of the magnet. With such an approach the patient table 130 can be placed into a safe position 340 from which the neonate 110 is moved and prepared for MR scanning. With an incubator in safe position 340 the neonate 110 may be moved towards MR scanner 102 along an axial route 380. Alternatively, the incubator can be placed in an alternate safe position such as 340a and the neonate 110 may be moved to the transfer station 200 along an alternate route such as 380a. Once the neonate is prepared for MR scanning, it can be moved together with the patient table into the isocenter 320 of the MR scanner 102.

Figure 4:
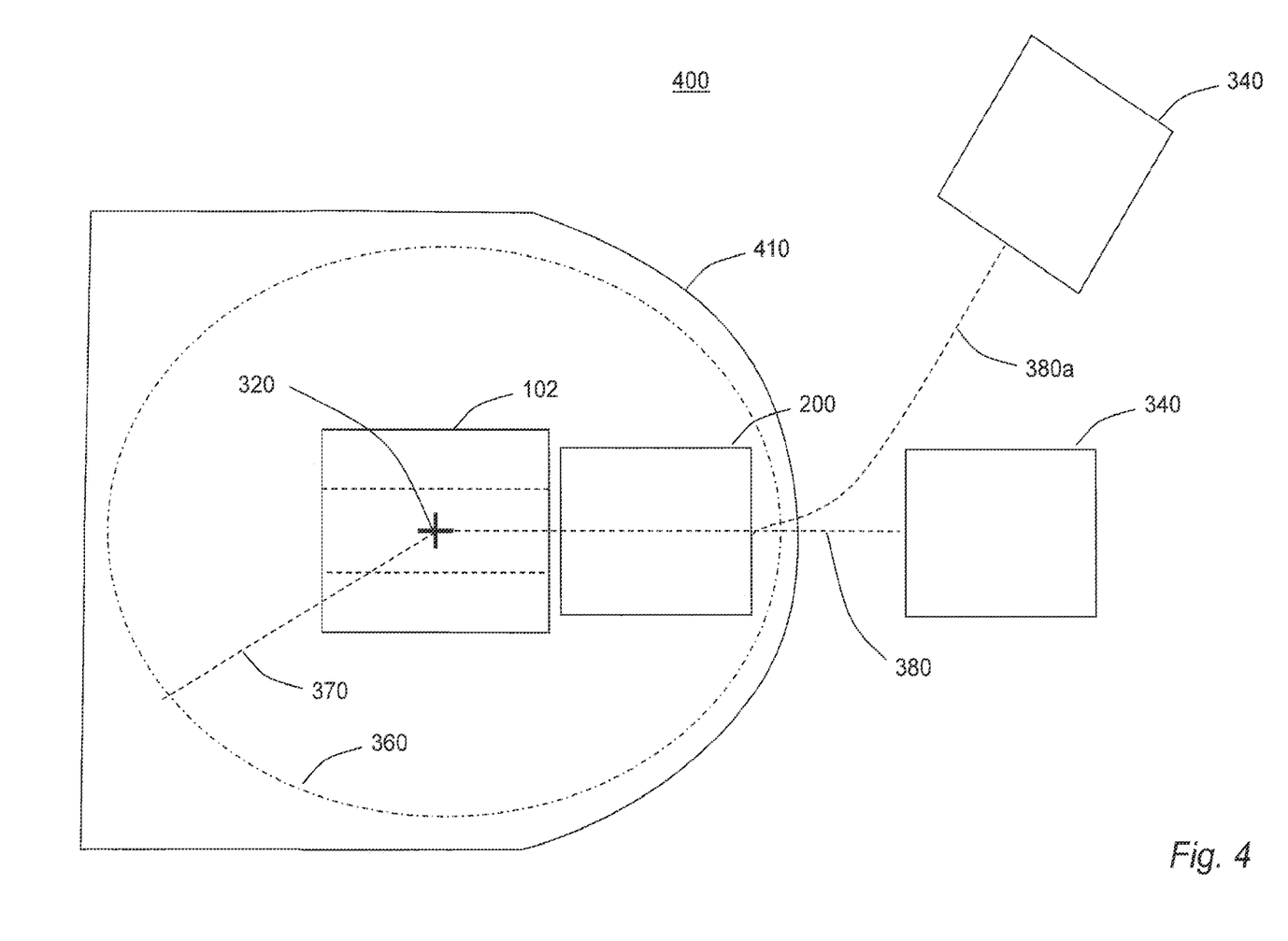
FIG. 4 is a top plan view of an exemplary MR magnet with an elevated floor barrier to limit access to the magnet.

Alternatively, the barrier can be augmented with a step design as shown in FIG. 4 in which the floor that accommodates the NICU incubator is lower than a raised floor 410 surrounding the magnet. The step created by the two levels of the floor acts to prevent the incubator from approaching too close to the magnet.

The patient table 130 may in one embodiment, as shown in FIG. 1, be open like an isolette. In one embodiment, the open isolette may be configured with radiant heating. In another embodiment, the transfer station may be enclosed like an incubator with the addition of a cover. In one embodiment, the enclosed transfer station may be configured to provide warm circulating air.

As mentioned, in one embodiment, patient table 130 may be equipped to include all necessary life support and monitoring equipment. Such equipment includes, but is not limited to, EKG monitoring, IV tubes, oxygen monitors, ventilators, breathing gases, and bilirubin treatment. If needed, patient table 130 can be powered by an external supply or an on-board MR-compatible battery. Alternatively, the patient table 130 may be manually advanced or extended as desired.

In one embodiment of the disclosure, patient table 130 may include physical barriers to prevent extraneous objects being sucked into the infant when the infant is inside the magnet. In one embodiment, the barrier may include a substantially full enclosure made of clear engineering plastic that is resistant to impact damage. This arrangement may provide full visual access of the baby but may provide a barrier to the entry of other objects into the magnet.

In one embodiment, a Faraday cage may be built into patient table 130 to prevent RF interference from degrading the MR image. This would be particularly advantageous if the MR system is not placed in an RF screen room. Should a Faraday cage be incorporated into the transfer station, an internal rf tight panel or door may be added between the magnet and the transfer station. It may also be desirable to provide penetration filters for monitoring leads to minimize rf interference during MR imaging.

In an even further embodiment, the transfer station may incorporate a scale for weighing the infants.

While the foregoing description includes many details and specificities, it is to be understood that these have been included for purposes of explanation only, and are not to be interpreted as limitations of the present disclosure. It will be apparent to those skilled in the art that other modifications to the embodiments described above can be made without departing from the spirit and scope of the disclosure. Accordingly, such modifications are considered within the scope of the disclosure as intended to be encompassed by the following claims and their legal equivalents.

What is claimed is:

1. A patient table for transferring neonatal infants to an MR scanner for imaging, comprising:
   a support table having at least one vertical support structure and an extendable, MR-compatible patient bed coupled to the support table, the support table supporting the extendable, MR-compatible patient bed at a vertical level of a scanning bore of an MR scanner; and
   an extending assembly coupled to at least one of the support table and the extendable, MR-compatible patient bed, the extending assembly being activatable to extend the extendable, MR-compatible patient bed into the scanning bore in an extended position and retract the extendable, MR-compatible patient bed from the scanning bore in a retracted position;
   wherein the extendable, MR compatible patient bed extends substantially perpendicularly from the at least one vertical support structure of the support table when in the extended position and rests atop the support table when in the retracted position.

2. The patient table of claim 1, wherein the MR-compatible patient bed comprises an at least partially releasably attached cover.

3. The patient table of claim 2, wherein the cover is configured to be releasably locked to the neonate-supporting portion of the MR-compatible patient bed.

4. The patient table of claim 1, wherein MR-compatible patient bed is configured to support an MR receive coil.

5. The patient table of claim 2, wherein the MR-compatible patient bed contains at least one access through which monitoring equipment may reach the neonate-supporting portion of the MR-compatible patient bed.

6. The patient table of claim 1, wherein the MR-compatible patient bed contains at least one electrical connection for attaching monitoring equipment to a neonate.

7. The patient table of claim 2, wherein the cover includes one or more access ports.

8. The patient table of claim 1, wherein the MR-compatible patient bed is configured to adjustably stabilize a neonate for MR scanning.

9. The patient table of claim 1, further comprising environmental controls for controlling at least one of the temperature or humidity.

10. The patient table of claim 1, wherein the MR-compatible patient bed includes a temperature sensor coupled to a controller that, when signaled, adjusts the temperature in the MR-compatible patient bed.

11. The patient table of claim 1, further comprising life support equipment.

12. The patient table of claim 11, wherein the life support equipment includes one or more of an EKG monitor, an IV tube, an oxygen monitor, a ventilator tube, compressed oxygen, or bilirubin treatment.

13. The patient table of claim 1, wherein the support table is electrically connected to an AC power supply.

14. The patient table of claim 1, further comprising a battery configured to power one or more of life support equipment, monitoring equipment, a temperature sensor, or a controller.

15. The patient table of claim 1, further comprising a scale for weighing a neonate.

16. The patient table of claim 1, further comprising wheels coupled to the support table for moving the patient table.

17. A system for MR scanning neonates in a NICU, comprising
   an MR scanner disposed in a neonatal intensive care unit, the MR scanner including an MR magnet having a sufficiently small size and sufficiently low magnetic flux density for being disposed within a neonatal intensive care unit; and
   a patient table for transferring a neonatal infant into a scanning bore of the MR scanner, the patient table comprising:
      a support table having at least one vertical support structure and an extendable, MR-compatible patient bed coupled to the support table, the support table supporting the extendable, MR-compatible patient bed at a vertical level of a scanning bore of an MR scanner; and
      an extending assembly coupled to at least one of the support table and the extendable, MR-compatible patient bed, the extending assembly being activatable to extend the extendable, MR-compatible patient bed into the scanning bore in an extended position and retract the extendable, MR-compatible patient bed from the scanning bore in a retracted position;
      wherein the extendable, MR compatible patient bed extends substantially perpendicularly from the at least one vertical support structure of the support table when in the extended position and rests atop the support table when in the retracted position.

18. The patient table of claim 17, wherein the MR-compatible patient bed comprises an at least partially releasably attached cover.

19. The patient table of claim 18, wherein the cover is configured to be releasably locked to the neonate-supporting portion of the MR-compatible patient bed.

20. The patient table of claim 1, wherein MR-compatible patient bed is configured to support an MR receive coil.

\* \* \* \* \*